US010302623B2

(12) United States Patent
Kukita

(10) Patent No.: US 10,302,623 B2
(45) Date of Patent: May 28, 2019

(54) FLUID SENSING VIBRATION SENSOR

(71) Applicant: NIHON DEMPA KOGYO CO., LTD., Tokyo (JP)

(72) Inventor: Hiroyuki Kukita, Saitama (JP)

(73) Assignee: NIHON DEMPA KOGYO CO., LTD., Tokyo (JP)

( * ) Notice: Subject to any disclaimer, the term of this patent is extended or adjusted under 35 U.S.C. 154(b) by 144 days.

(21) Appl. No.: 15/511,233

(22) PCT Filed: Aug. 12, 2015

(86) PCT No.: PCT/JP2015/072845
§ 371 (c)(1),
(2) Date: Mar. 14, 2017

(87) PCT Pub. No.: WO2016/042950
PCT Pub. Date: Mar. 24, 2016

(65) Prior Publication Data
US 2017/0284997 A1    Oct. 5, 2017

(30) Foreign Application Priority Data

Sep. 19, 2014  (JP) ................................ 2014-191438

(51) Int. Cl.
*G01N 33/487* (2006.01)
*G01N 29/02* (2006.01)
*G01N 29/24* (2006.01)
*G01N 29/036* (2006.01)
*G01N 9/00* (2006.01)

(52) U.S. Cl.
CPC ....... *G01N 33/48785* (2013.01); *G01N 9/002* (2013.01); *G01N 29/022* (2013.01); *G01N 29/036* (2013.01); *G01N 29/2443* (2013.01); *G01N 29/2437* (2013.01); *G01N 2291/0256* (2013.01)

(58) Field of Classification Search
CPC .... G01N 29/022; G01N 9/002; G01N 29/036; G01N 29/2443; G01N 29/2437; G01N 33/48785
USPC ............ 73/24.01, 32 A, 54.24, 54.41, 61.45, 73/61.79, 64.53
See application file for complete search history.

(56) References Cited

FOREIGN PATENT DOCUMENTS

| JP | H03-188350 A | 8/1991 |
| JP | H09-145583 A | 6/1997 |
| JP | 2004-069686 A | 3/2004 |

(Continued)

OTHER PUBLICATIONS

"International Search Report (Form PCT/ISA/210) of PCT/JP2015/072845", dated Oct. 27, 2015, with English translation thereof, pp. 1-4.

Primary Examiner — Helen C Kwok
(74) Attorney, Agent, or Firm — JCIPRNET

(57) ABSTRACT

One side of the surfaces of the crystal resonator 4 including an adsorbing film 46 that absorbs a sensing object on an excitation electrode 42A is pressed with the channel forming member 5 using the upper-side cover body 21 to form a channel 57, which runs from one end side to the other end side on one side of surfaces of the crystal resonator 4. A depressed portion 84 is disposed in at least one of: a position opposed to the channel 57 and at a surface on an opposite side of the channel 57 in the channel forming member 5, and a position opposed to the channel 57 and at a surface on the opposite side of the channel 57 in the pressing member with respect to the channel forming member 5.

3 Claims, 9 Drawing Sheets

(56) References Cited

FOREIGN PATENT DOCUMENTS

| | | |
|---|---|---|
| JP | 2011-027716 A | 2/2011 |
| JP | 2012-145566 A | 8/2012 |
| JP | 2015-068747 A | 4/2015 |
| JP | 2015-197330 A | 11/2015 |

FLUID SENSING VIBRATION SENSOR

CROSS-REFERENCE TO RELATED APPLICATION

This application is a 371 application of the International PCT application serial no. PCT/JP2015/072845, filed on Aug. 12, 2015, which claims the priority benefits of Japan Patent Application No. 2014-191438, filed on Sep. 19, 2014. The entirety of the above-mentioned patent application is hereby incorporated by reference herein and made a part of this specification.

TECHNICAL FIELD

The disclosure relates to a sensing sensor for sensing a sensing object contained in a sample solution based on oscillation frequency of piezoelectric resonator.

BACKGROUND ART

In a clinical field, a simple method called Point of Care TEST (POCT), which is typified by a self-monitoring of blood glucose level, for example, is spreading. As an example of this method, Patent Document 1 describes a sensing sensor using Quartz Crystal Microbalance (QCM) and discloses a structure that forms a housing space for a sample solution between an upper-side case and a crystal resonator by placing the crystal resonator on a wiring board and engaging the upper-side case and a lower-side case with each other. As a sensitivity enhancing technique of QCM, there are twin sensors that perform a differential measurement. This technique forms two electrodes symmetrically with respect to a channel on one crystal such that the sample solution simultaneously and similarly flows with respect to the electrodes to cancel ambient external noise.

With a sensing sensor, it is desired to narrow a height of a channel to improve a contact ratio of a sensing object to a surface of a crystal resonator. Patent Document 2 describes a structure that configures a height of a channel to 0.2 mm. However, shape variations of a fitted cover may collapse the channel or break the crystal resonator when a channel forming member is pressed. A method that reduces a pressure from the cover that is fitted by narrowing a depressed portion of a seat may be possible, but a sample solution may leak outside the sensor.

Patent Document 3 discloses a method for constituting a piezoelectric sensor by: disposing a piezoelectric resonator on a lower case including an opening portion and a groove surrounding the opening portion, forming protrusions corresponding to a sample solution injection port and the groove in the upper case, and fitting the groove of the lower case and the protrusions of the upper case. However, this document does not mention a height of a channel for a sample solution on the piezoelectric resonator. Accordingly, a problem to be solved differs from the disclosure.

CITATION LIST

Patent Document

Patent Document 1: Japanese Unexamined Patent Application Publication No. 2012-145566
Patent Document 2: Japanese Unexamined Patent Application Publication No. 2011-27716
Patent Document 3: Japanese Unexamined Patent Application Publication No. H9-145583

SUMMARY OF THE DISCLOSURE

Problems to be Solved by the Disclosure

The disclosure has been made under such circumstances, and an object thereof is to provide a sensing sensor that ensures an improved measurement sensitivity of a sensing object by lowering a height of a sample solution providing space.

Solutions to the Problems

A sensing sensor of the disclosure includes a wiring board, a piezoelectric resonator, a channel forming member, and a pressing member. A wiring board has one surface side on which a depressed portion is formed. The piezoelectric resonator includes a piezoelectric piece on which an excitation electrode electrically connected to a conductive path of the wiring board is disposed. The piezoelectric resonator has one surface side on which an adsorbing film that adsorbs a sensing object in a sample solution is formed. The piezoelectric resonator is secured to the wiring board in a state where a vibrating region is opposed to the depressed portion to cover the depressed portion. The channel forming member is disposed to cover a region in the one side of the wiring board including the piezoelectric resonator. The channel forming member forms a channel between the piezoelectric resonator and the channel forming member and the channel communicates with an injection port of the sample solution. The pressing member presses a surface on an opposite side of the wiring board in the channel forming member to press the channel forming member against the wiring board. The sensing sensor is configured to form a clearance between the pressing member and a portion on an opposite side of the channel in the channel forming member to prevent the channel from being collapsed when the pressing member presses the channel forming member.

The sensing sensor of the disclosure may include a crush margin that buffers a pressure by changing a shape thereof due to a pressure of the pressing member on a surface on the opposite side of the channel in the channel forming member to prevent the channel from being collapsed when the pressing member presses the channel forming member. The sensing sensor of the disclosure may include a crush margin disposed on a surface on the wiring board side in the channel forming member, the crush margin being disposed to project from a surface contacting one side of the surfaces of the wiring board including the piezoelectric resonator in the channel forming member when the pressing member presses the channel forming member.

Effects of the Disclosure

A sensing sensor of the disclosure includes a channel and a depressed portion. One side of the surfaces of the crystal resonator including an adsorbing film that absorbs a sensing object on an excitation electrode is pressed with the channel forming member using a pressing member to form the channel, which runs from one end side to the other end side on one side of surfaces of the crystal resonator. The depressed portion is disposed in at least one of: a position opposed to the channel and at a surface on an opposite side of the channel in the channel forming member, and a position opposed to the channel and at a surface on the opposite side of the channel in the pressing member with respect to the channel forming member. Therefore, even in the case where the pressing member has a distortion, a deformation of the channel is inhibited when the channel forming member is pressed. Accordingly, a sample solution stably flows in the channel to improve a measurement sensitivity.

DESCRIPTION OF PREFERRED EMBODIMENTS

The following describes a sensing device using a sensing sensor according to an embodiment of the disclosure. This sensing device uses a microfluidic chip. The sensing device is configured to detect, for example, presence/absence of an antigen, such as virus, in a sample solution obtained from nasal cavity swab of a human so as to determine whether the human has been infected with virus or not with the microfluidic chip. As illustrated in an external perspective view in FIG. 1, the sensing device includes a main body 12 and a sensing sensor 2. The sensing sensor 2 is attachably/detachably connected to an insertion port 17 that is formed in the main body 12. The main body 12 includes, for example, a display 16 constituted by a liquid crystal display screen on a top surface. The display 16 displays, for example, an output frequency of an oscillator circuit, which is disposed in the main body 12 and will be described later, a measurement result, such as an amount of frequency transition, presence/absence of detected virus or a similar result.

Figure 1:
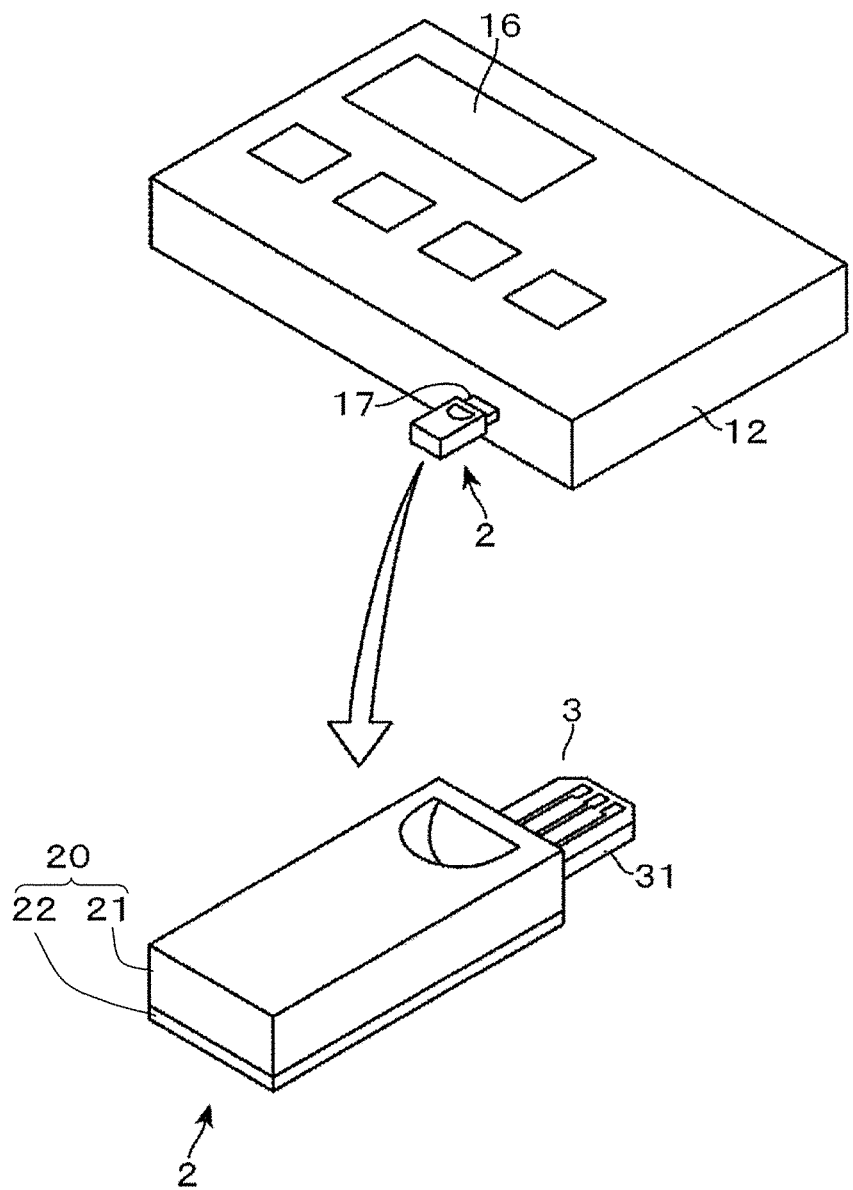
FIG. 1 is a perspective view of a sensing device and a sensing sensor according to the disclosure.
Figure 2:
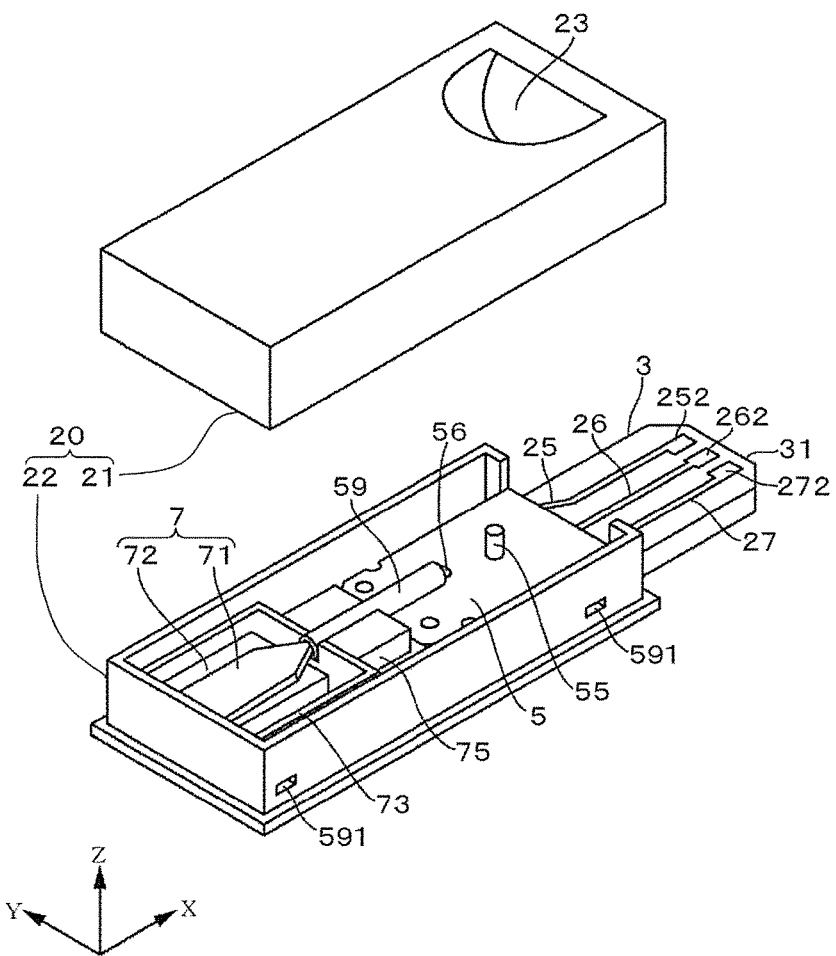
FIG. 2 is an exploded perspective view of the sensing sensor.
Figure 3:
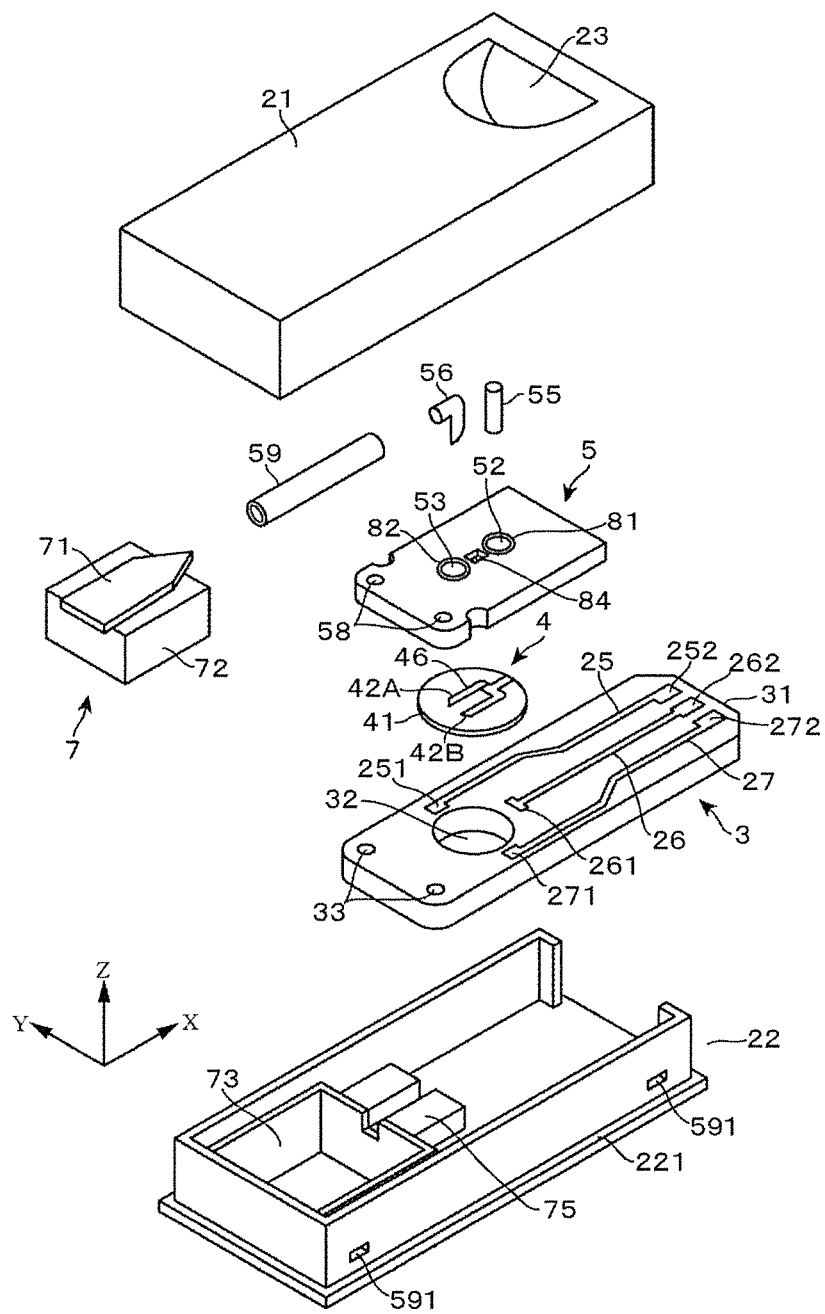
FIG. 3 is an exploded perspective view illustrating a top surface side of respective portions of the sensing sensor.
Figure 4:
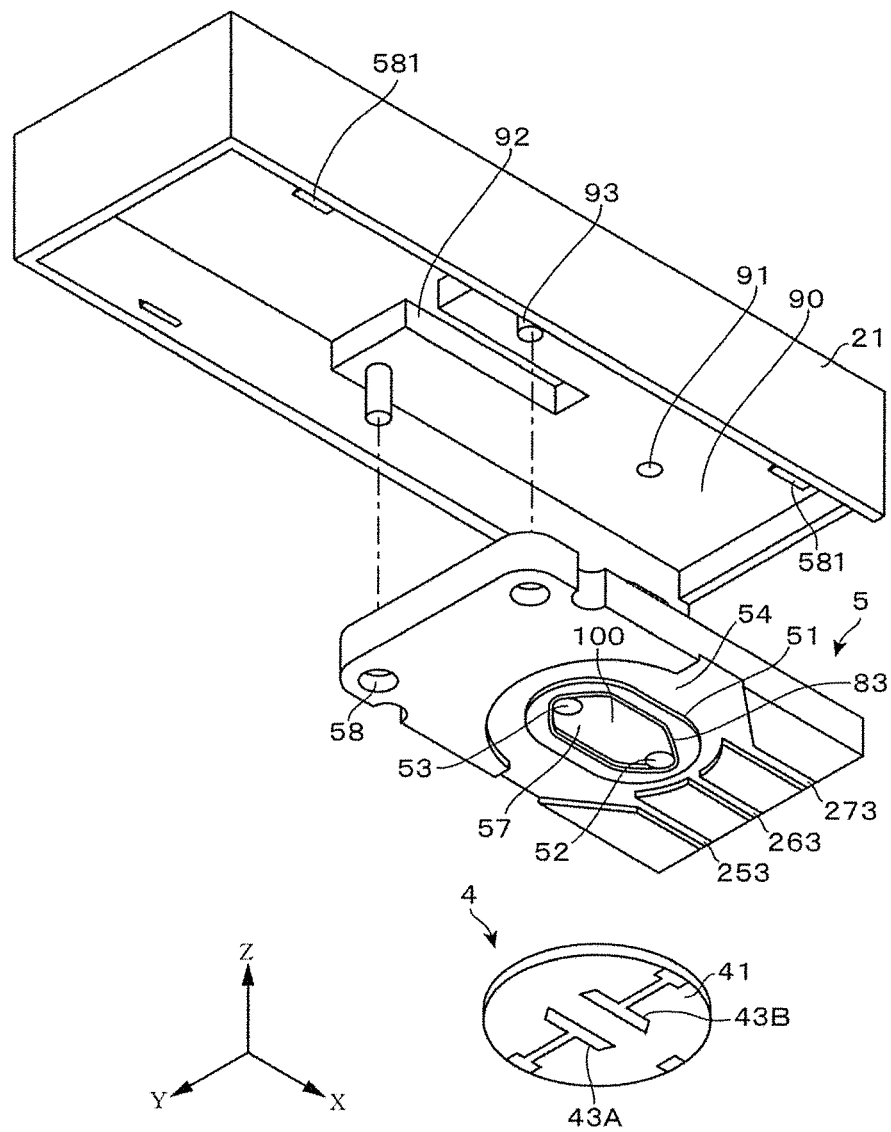
FIG. 4 is an exploded perspective view illustrating a lower surface side of a part of the sensing sensor.
Figure 5A:
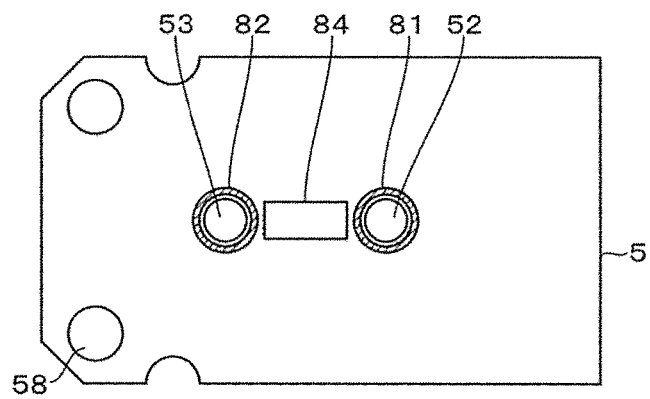
FIG. 5A, FIG. 5B and FIG. 5C are plan views and a vertical cross-sectional view of the top surface side and the lower surface side of a channel forming member.
Figure 5B:
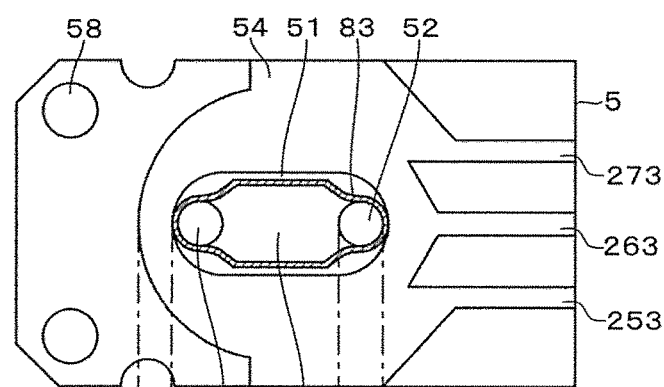
Figure 5C:
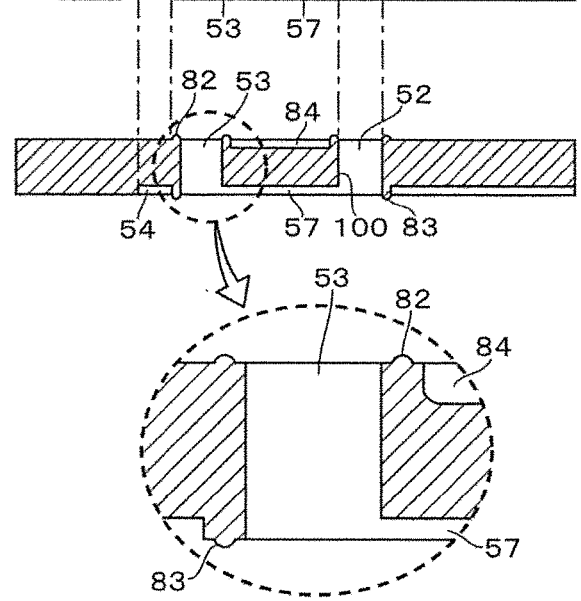
Figure 6:
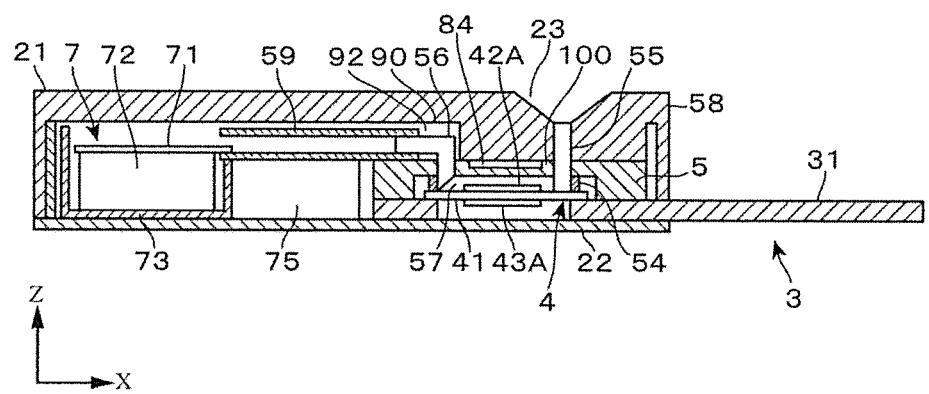
FIG. 6 is a longitudinal sectional side view of the sensing sensor.
Figure 7:
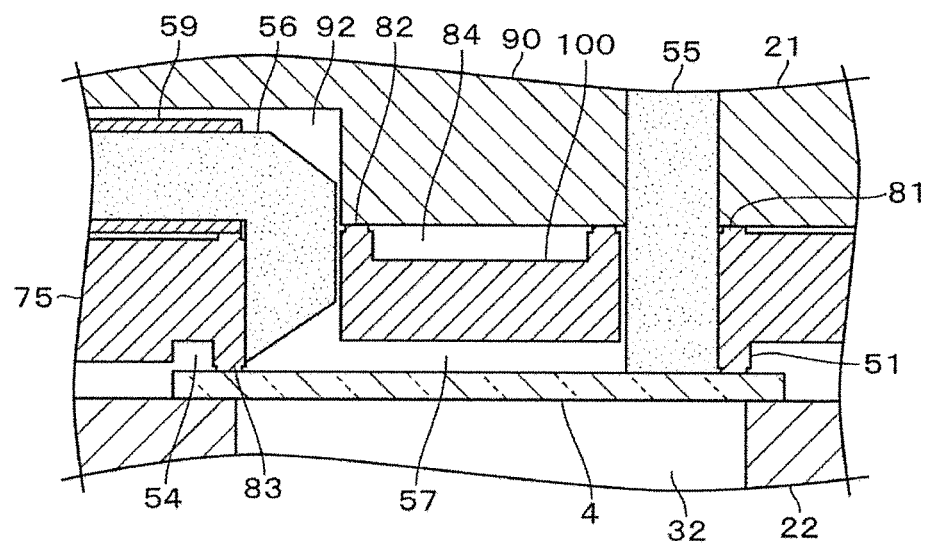
FIG. 7 is an enlarged longitudinal sectional side view of a channel of the sensing sensor.

Subsequently, the sensing sensor 2 will be described. FIG. 2 is a perspective view illustrating the sensing sensor 2, which is illustrated in FIG. 1, in a state where an upper-side cover body 21 is removed. FIG. 3 and FIG. 4 are respective perspective views illustrating a front side (top surface side) of each of members of the sensing sensor 2 and a back side (lower surface side) of some members. FIG. 5A illustrates a plan view illustrating the top surface side. FIG. 5B illustrates a plan view illustrating a lower surface side. FIG. 5C illustrates a vertical cross-sectional view of a channel forming member 5. FIG. 6 illustrates a vertical cross-sectional view of the sensing sensor 2. FIG. 7 is a drawing in which a channel 57 is enlarged. The sensing sensor 2 includes a container 20 constituted of the upper-side cover body 21 and a lower-side case body 22 as illustrated in FIG. 1. A wiring board 3 with a shape extended in a longitudinal direction is arranged over the lower-side case body 22, and an insertion portion 31 that is inserted into the insertion port 17 of the above-described main body 12 is formed at one end side of the longitudinal direction in the wiring board 3. In the following description, the insertion portion 31 side of the sensing sensor 2 denotes the rear, and the other end side denotes the front.

At the position of the front side of the wiring board 3, a through hole 32 is formed. The wiring board 3 is arranged such that the bottom surface of the lower-side case body 22 covers the through hole 32, and the insertion portion 31 protrudes outside the lower-side case body 22. The wiring board 3 includes three wirings 25 to 27 extending in the longitudinal direction on its front surface side. In the insertion portion 31, terminal portions 252, 262, and 272 are formed at the one end side of the respective wirings 25 to 27, respectively. In the outer edge of the through hole 32, terminal portions 251, 261 and 271 are formed in the other end side of the respective wirings 25 to 27, respectively. Further, in the further front of the through hole 32 in the wiring board 3, two hole portions 58 for locating the horizontal position of the wiring board 3 are formed alongside in the width direction.

Subsequently, a crystal resonator 4 will be described. The crystal resonator 4 includes, for example, an AT-cut circular plate-shaped crystal element 41. On a front surface side and a back surface side of the crystal element 41, two pairs of excitation electrodes 42A and 43A, and 42B and 43B, which are formed of, for example, Au (gold), are disposed in a strip shape. The excitation electrodes 42A and 42B on a top surface side are combined and connected to earth. On a surface of the excitation electrode 42A on one side, an adsorbing film 46, which is constituted with an antibody for adsorb a sensing object as an antigen, for example, is formed. A surface of the excitation electrode 42B on the other side is in an exposed state without having the adsorbing film 46 formed. As illustrated in FIG. 3, the crystal resonator 4 is disposed such that the excitation electrodes 43A and 43B on the back surface side face the through hole 32 of the wiring board 3, to be bonded with a conductive adhesive. In view of this, the excitation electrodes 43A and 43B on the back surface side of the crystal resonator 4 are connected to the wirings 25 and 27, respectively, and the excitation electrodes 42A and 42B on the front surface side are connected to the wiring 26.

Returning to FIG. 3, the channel forming member 5 is arranged on the top surface side of the wiring board 3. The channel forming member 5 is constituted with a plate-shaped member made of, for example, polydimethylsiloxane (PDMS). In the position near to the front of the channel forming member 5, the hole portions 58 for positioning the channel forming member 5 are arranged at the position corresponding to hole portions 33 arranged in the wiring board 3 such that the hole portions 58 pass through the channel forming member 5 in the thickness direction.

Describing with reference to FIG. 5A that illustrates the top surface side, FIG. 5B that illustrates the lower surface side, and FIG. 5C that illustrates the vertical cross-sectional view of the channel forming member 5, a circular-shaped depressed portion 54 is provided so as to house the crystal resonator 4 in the lower surface side of the channel forming member 5. On the lower surface side of the channel forming member 5, grooves 253, 263, and 273 are formed to each communicate with the depressed portion 54 and to house the respective wirings 25 to 27 formed in the wiring board 3. In the depressed portion 54, a surrounding portion 51 is arranged to partition and form the channel 57 for the sample solution with the front surface of the crystal resonator 4 when the channel forming member 5 is pressed to the wiring board 3 side. This surrounding portion 51 is constituted with an annular protrusion the outer edge of which is formed in an oval shape, such that the longitudinal direction of the surrounding portion 51 aligns with the front-rear direction of the sensing sensor 2. The surrounding portion 51 is constituted so as to protrude from the depressed portion 54 with a thickness of 300 μm, and the inside region of the surrounding portion 51 has a plane with a height identical to a height of the depressed portion 54. The channel forming member 5 includes through holes 52 and 53 that have openings at the rear end and the front end of the channel 57, respectively, and pass through the channel forming member 5 in the thickness direction. The channel 57 is constituted to gradually expand its width from the position of each of the through holes 52 and 53.

In peripheral areas of the respective through holes 52 and 53 on the top surface side of the channel forming member 5, annular-shaped crush margins 81 and 82 with cross-sectional surfaces in cut off oval shapes are formed to surround the respective through holes 52 and 53. In the channel forming member 5, the crush margins 81 and 82 are formed to project by 0.05 mm from a surface facing a surface that presses the channel forming member 5 of the upper-side cover body 21. Thus, a pressure that the channel forming member 5 receives from the upper-side cover body 21 is buffered. As illustrated in FIG. 5A, FIG. 5B and FIG. 5C, on the lower surface of the surrounding portion 51 in the channel forming member 5, an annular-shaped crush margin 83 with a cross-sectional surface in a cut off oval shape is formed along an inner edge in the lower surface of the surrounding portion 51. The crush margin 83 is formed to project by 0.05 mm from a surface facing the crystal resonator 4 of the surrounding portion 51 when the upper-side cover body 21 and the lower-side case body 22 are locked with one another to press the channel forming member 5 against the wiring board 3. Thus, a pressure from the channel forming member 5 to the crystal resonator 4 is buffered. Furthermore, between the through holes 52 and 53 on the top surface side of the channel forming member 5, an approximate rectangular-shaped depressed portion 84 having 500 μm in depth is formed so as to be opposed to the channel 57.

The hole portions 58 of the channel forming member 5 are arranged so as to align the hole portions 33 disposed in the wiring board 3. Then, the surrounding portion 51 is disposed on the top surface of the crystal resonator 4. The excitation electrodes 42A and 42B are aligned and housed in the center of the channel 57. The lower surface side of the channel 57 is covered with the crystal resonator 4. This region surrounded by the surrounding portion 51 and the crystal resonator 4 has the bottom surface constituted of the crystal resonator 4 to form the channel 57 of 300 μm in depth with a ceiling surface and the bottom surface extending in parallel.

The through holes 52 and 53, as illustrated in FIG. 3, attachably/detachably include an inlet-side capillary member 55 and an outlet-side capillary member 56 each constituted of a porous member. The inlet-side capillary member 55, for example, is a columnar member and constituted of a chemical fiber bundle, such as polyvinyl alcohol (PVA). The inlet-side capillary member 55 is disposed so as to cover the through hole 52. An upper end of the inlet-side capillary member 55 is disposed to be exposed to an injection port 23 formed in the upper-side cover body 21, which will be described later, and the lower end is disposed to enter into the channel 57. Similarly, the outlet-side capillary member 56 is constituted of a chemical fiber bundle, such as polyvinyl alcohol (PVA), and is formed to be an L-shape by extending upward then bending to extend horizontally. The outlet-side capillary member 56 is disposed so as to cover the through hole 53 and a lower end of the outlet-side capillary member 56 is disposed to enter into the channel 57. Furthermore, the lower end of the outlet-side capillary member 56 is inclined to the front side from the rear side.

The other end side of the outlet-side capillary member 56 is connected to one end side of an effluent channel 59 constituted of, for example, a hydrophilic glass tube. The other end side of the effluent channel 59 is connected to an effluent absorbing portion 7 constituted of, for example, a capillary sheet 71, which suctions liquid flown from the effluent channel 59, and an absorbing member 72, which absorbs liquid suctioned by the capillary sheet 71. A case body 73 to prevent a liquid leakage from the absorbing member 72 is disposed outside the effluent absorbing portion 7. Reference numeral 75 in the drawing denotes a supporting member that supports the effluent channel 59.

The upper-side cover body 21, which corresponds to a pressing member, is disposed so as to cover the wiring board 3 except for the insertion portion 31, the channel forming member 5, and the effluent absorbing portion 7 from the upper side. The top surface side of the upper-side cover body 21 includes the injection port 23 inclined in a cone shape. The back surface side of the upper-side cover body 21 includes a pressing portion 90 for pressing the channel forming member 5 against the wiring board 3. The pressing portion 90 is constituted to be, for example, an approximate box shape and presses an entire top surface of the channel forming member 5 vertically downward with its lower surface when the upper-side cover body 21 is engaged and locked together with the lower-side case body 22. The pressing portion 90 includes a through hole 91 passing through to the injection port 23 at the position corresponding to the through hole 52. A cutout 92 to ensure an installation area for the effluent channel 59 and the outlet-side capillary member 56 is formed toward the front side from the position corresponding to the through hole 53. The pressing portion 90 includes fixing pillars 93, which are inserted in the hole portions 58 and 33 disposed in the channel forming member 5 and the wiring board 3, respectively, and are for positioning the channel forming member 5 and the wiring board 3. The upper-side cover body 21 internally includes claws 581. Engaging the claws 581 with grooves 591, which are formed to correspond, of the lower-side case body 22 constitutes a locking structure of the upper-side cover body 21 and the lower-side case body 22.

The following describes the channel 57 when the channel forming member 5 is pressed against the wiring board 3 with the upper-side cover body 21 in the sensing sensor 2. Since the excitation electrodes 42A, 42B, 43A, and 43B and the respective wirings 25 to 27 are extremely thin compared with the thickness of the crystal resonator 4, the crystal resonator 4 is illustrated to be one flat plate in FIG. 6 to FIG. 11. As illustrated in FIG. 6 and FIG. 7, after disposing each of the components inside the lower-side case body 22, the upper-side cover body 21 covers the lower-side case body 22. Then the upper-side cover body 21 is pressed against the lower-side case body 22 until the claws 581 of the upper-side cover body 21 engage with the grooves 591 in the side surface of the lower-side case body. The channel forming member 5 at this time is pressed against the wiring board 3 with the top surface being pressed with the pressing portion 90 inside the upper-side cover body 21 as illustrated in FIG. 6 and FIG. 7.

Figure 8:
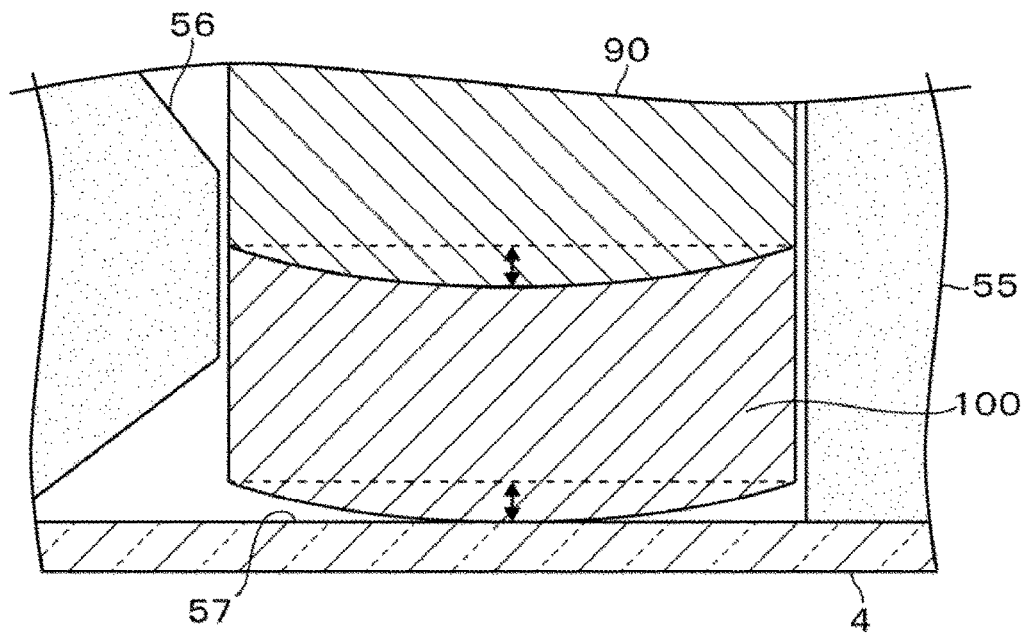
FIG. 8 is an explanatory drawing describing a channel in a conventional sensing sensor.
Figure 9:
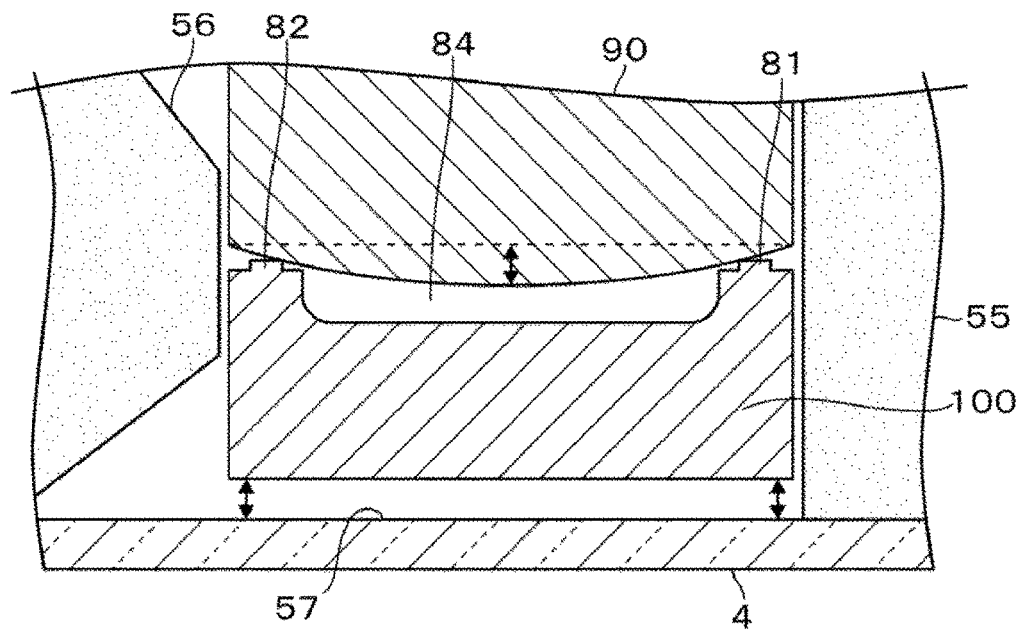
FIG. 9 is an explanatory drawing describing a channel of a sensing sensor according to an embodiment of the disclosure.

Assuming that a portion of the channel forming member 5 above a supply channel is a ceiling portion 100, in the case where the depressed portion 84 is not disposed on the top surface side of the channel forming member 5, a center portion of the ceiling portion 100 is strongly pressed when a distortion is generated in the upper-side cover body 21, for example, when a vicinity of a center portion of the pressing portion 90 is lowered. Therefore, the ceiling portion 100 curves conforming to a shape of the pressing portion 90. In this example, the ceiling portion 100 curves such that the central portion of the ceiling portion 100 is pressed down. Thus, the channel 57 possibly collapses as illustrated in FIG. 8. In the case where the depressed portion 84 is disposed on the top surface of the channel forming member 5 so as to be opposed to the channel 57 like the channel forming member 5 according to the embodiment of the disclosure, the depressed portion 84 does not contact the pressing portion 90 even when the pressing portion 90 is not plane. Therefore, the ceiling portion 100 does not curve along the shape of the pressing portion 90 to ensure the ceiling surface of the channel 57 keeping a posture parallel to the crystal resonator 4. Accordingly, collapsing of the channel 57 can be inhibited as illustrated in FIG. 9.

Figure 10:
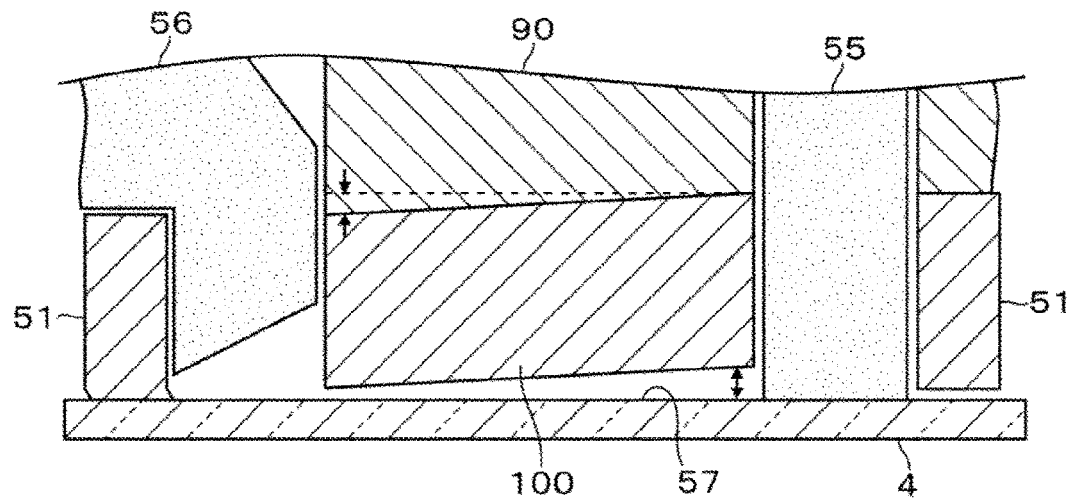
FIG. 10 is an explanatory drawing describing a channel in a conventional sensing sensor.
Figure 11:
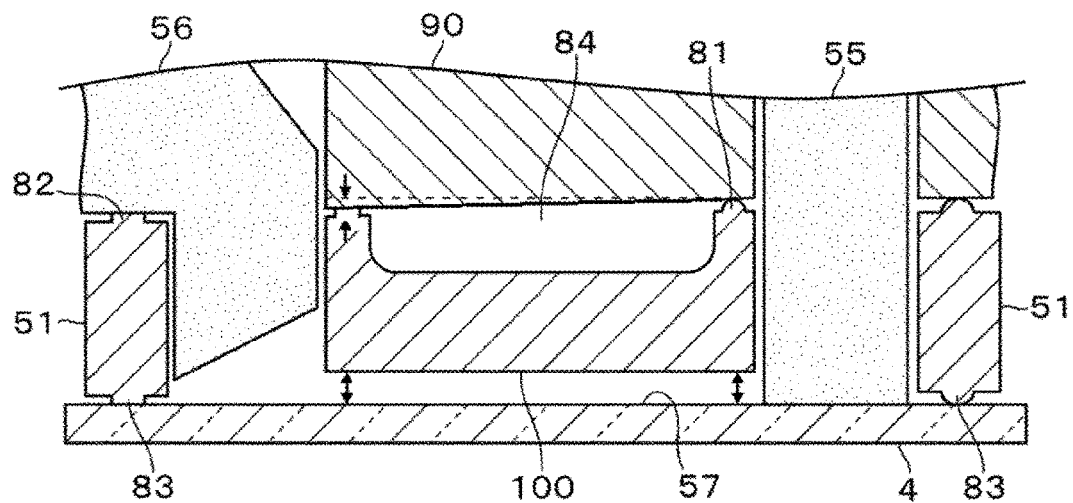
FIG. 11 is an explanatory drawing describing a channel of a sensing sensor according to an embodiment of the disclosure.

For example, in the case where the front side of the pressing portion 90 is low compared with the rear side, when the channel forming member 5 without the crush margins 81 and 82 on the top surface side is pressed and secured, the front side receives a stronger pressing force than a pressing force received by the rear side in the ceiling portion 100 of the channel 57 as illustrated in FIG. 10. Thus, there is a case where the channel 57 is covered by the front side of the ceiling portion 100 in the supply channel being pressed down. In the case where the crush margins 81 and 82 are disposed in the peripheral areas of the through holes 52 and 53 on the top surface side of the channel forming member 5, the crush margin 82 formed in the peripheral area of the through hole 53 in the front side on the top surface side of the channel forming member 5 is crushed as illustrated in FIG. 11, thereby inhibiting the front side of the ceiling portion 100 of the channel 57 from being pressed down. Accordingly, the ceiling surface of the channel 57 and the crystal resonator 4 form a parallel posture to inhibit collapsing of the channel 57.

Subsequently, the crush margin 83 disposed on the lower surface side of the channel forming member 5 will be described. As illustrated in FIG. 10, in the case where the crush margin 83 is not disposed, there is possibly a distortion in the front side of the surrounding portion 51 or a gap between the surrounding portion 51 in the rear side and the crystal resonator 4 when the front side is strongly pressed and the pressure on the rear side is weak on the top surface of the channel forming member 5. Disposing the crush margin 83 on the lower surface side of the channel forming member 5 can inhibit a distortion of the surrounding portion 51 by the crush margin 83 being crushed when the pressure on the front side is strong and enhance an adhesion between the rear side of the surrounding portion 51 and the crystal resonator 4.

Figure 12:
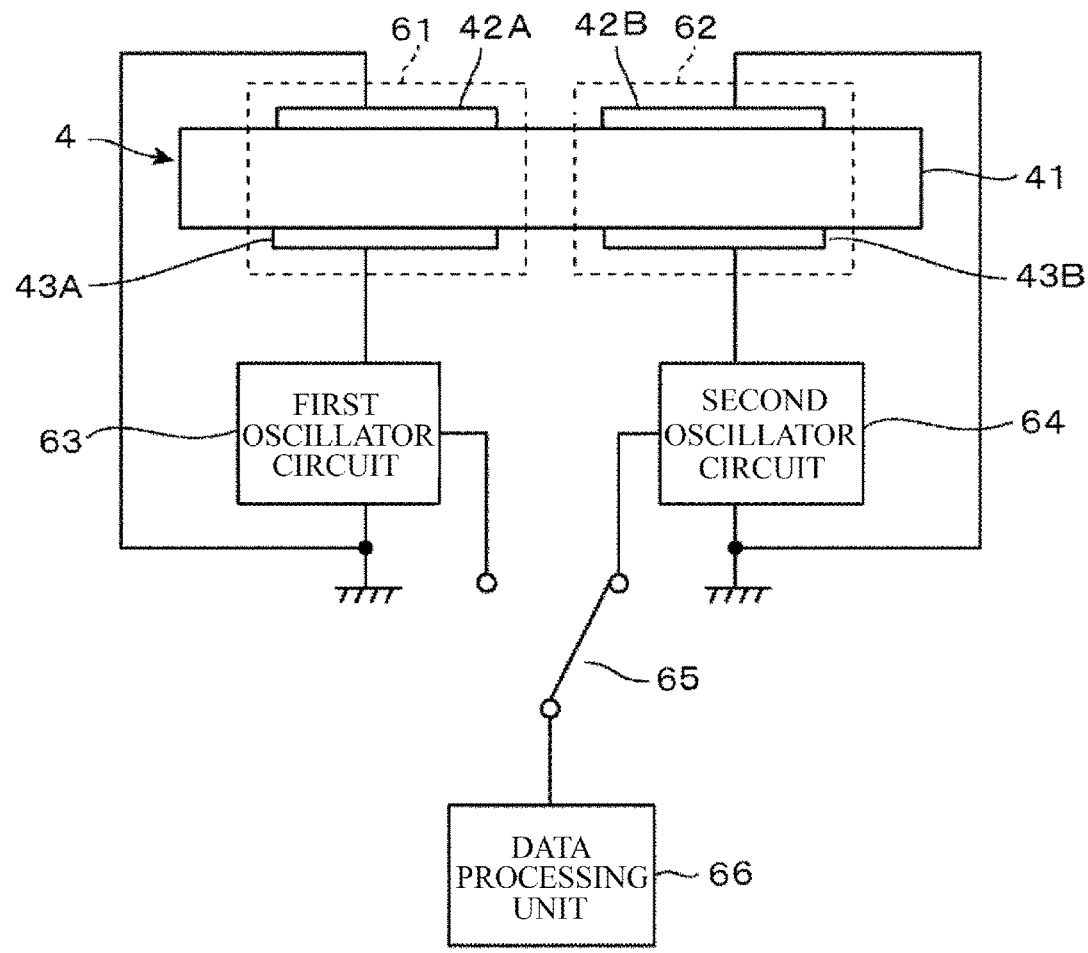
FIG. 12 is a schematic configuration diagram of the sensing device.

Subsequently, a description will be given of the whole configuration of the sensing device that uses the sensing sensor 2. Inserting the insertion portion 31 of the above-described sensing sensor 2 into the main body 12 electrically connects the terminal portions 252, 262, and 272 formed in the insertion portion 31 to connection terminal portions (not illustrated) formed in the main body 12 to correspond to these terminal portions 252, 262, and 272, and constitutes the sensing device. As illustrated in FIG. 12, a first oscillator circuit 63 and a second oscillator circuit 64 that are constituted, for example, with Colpitts circuits are arranged in the main body 12. The first oscillator circuit 63 is constituted to oscillate a first vibrating region 61, which is the region sandwiched between the excitation electrode 42A and the excitation electrode 43A in the crystal resonator 4, and the second oscillator circuit 64 is constituted to oscillate a second vibrating region 62, which is the region sandwiched between the excitation electrode 42B and the excitation electrode 43B. The terminal portion 262 is connected so as to be ground potential in oscillation. The surfaces of the first vibrating region 61 and the second vibrating region 62 in the front surface side correspond to measurement regions.

The output sides of the first and the second oscillator circuits 63 and 64 are connected to a switch 65, and a data processing unit 66 is arranged in the latter part of the switch 65. The data processing unit 66 performs a digitalizing process to a frequency signal that is an input signal, and obtains time-series data of an oscillation frequency "F1" output from the first oscillator circuit 63 and time-series data of an oscillation frequency "F2" output from the second oscillator circuit 64.

The sensing device of this invention performs intermittent oscillation by alternately switching a channel 1 connecting the data processing unit 66 to the first oscillator circuit 63 and a channel 2 connecting the data processing unit 66 to the second oscillator circuit 64 using the switch 65. Consequently, the sensing device ensures avoiding interference between the two vibrating regions 61 and 62 of the sensing sensor 2 and obtaining the stable frequency signals. Subsequently, these frequency signals are, for example, time-shared and fed into the data processing unit 66. The data processing unit 66 calculates the frequency signals as, for example, digital values, and then performs arithmetic processing based on the time-shared data of the calculated digital values, and then displays the arithmetic operation result, such as presence/absence of antigen, on the display 16.

A description will be given of a method for determining presence/absence of the sensing object in the sample solution by this sensing device. First the sensing sensor is connected to the main body 12, and a thinner, which is composed of, for example, saline and includes no sensing object, is dropped in the injection port 23 by use of an injector (not illustrated). The liquid is absorbed to the inlet-side capillary member by capillarity and flows inside this inlet-side capillary member 55, and then flows into the channel 57 to be supplied to the rear-side surface of the crystal resonator 4. Since the surface of the crystal element 41 constituting the crystal resonator 4 is hydrophilic, the liquid wets and expands inside the supply channel. Subsequently to the liquid expanding in the supply channel, the liquid in the inlet-side capillary member 55 is drawn out to the surface of the crystal element 41 by a surface tension, and thus the liquid continuously flows from the injection port 23 to the supply channel. The ceiling surface of the supply channel and the crystal resonator 4 are in parallel at this time. The width of the supply channel is constituted to radially expand from the rear side and to become a constant width in a midstream region, and to gradually narrow toward the outlet-side capillary member 56 afterward. Since the excitation electrodes 42A and 42B are arranged alongside near the midstream of the supply channel, the liquid simultaneously flows on the surface of the excitation electrodes 42A and 42B at a constant speed.

Subsequently, when the liquid on the surface of the crystal resonator 4 reaches the outlet-side capillary member 56, the liquid is absorbed into the outlet-side capillary member 56 by capillarity and flows inside this outlet-side capillary member 56 to exude out to the effluent channel 59. Here, due to workings of the principle of the siphon in addition to capillarity, the liquid that has been continuously and automatically supplied in a liquid receiving portion passes through the surface of the crystal resonator 4 to be discharged to the effluent channel 59.

The liquid inside the effluent channel 59 flows inside this effluent channel 59 to the downstream side and reaches the capillary sheet 71. When the liquid inside the effluent channel 59 reaches the capillary sheet 71, the liquid moves to the capillary sheet 71 side at a speed larger than the moving speed of the liquid that is flowing inside the effluent channel. When contacting the capillary sheet 71, the liquid expands and flows inside the capillary sheet 71 by capillarity to form a state where the liquid flow is discontinued inside the effluent channel 59.

When the liquid is separated inside the effluent channel 59, the liquid in the capillary sheet 71 side is absorbed into and retained in the absorbing member 72, which contacts the capillary sheet 71. Meanwhile, since the liquid remaining in the injection port 23 attempts to flow toward the effluent channel 59 by capillarity and the principle of siphon, this liquid flow causes the liquid remaining in the effluent channel 59 to move to the downstream side and contact the capillary sheet 71 again. Consequently, when all the liquid in the liquid receiving portion flows out after repeating the separation of the liquid and the flow of the liquid inside the effluent channel 59, the liquid stops in the state of being separated in the effluent channel 59.

Returning to a description of supplying a buffer solution, the buffer solution dropped into the injection port 23 flows inside the sensing sensor 2 as described above. When the buffer solution flowing in the channel 57 is supplied to the surface of the excitation electrodes 42A and 42B, these excitation electrodes 42A and 42B equally receive an influence of hydraulic pressure since they are symmetrically formed viewing from the inlet side to the outlet side of the supply channel. This equally reduces the oscillation frequencies of both the first vibrating region 61 and the second vibrating region 62.

Subsequently, the sample solution with an amount identical to the buffer solution is supplied to the injection port 23. This increases a pressure applied to the buffer solution absorbed in the inlet-side capillary member 55 and causes this buffer solution to flow toward the downstream side inside the effluent channel 59 again, and thus the sample solution is absorbed into the inlet-side capillary member 55. The absorbed sample solution flows into the channel 57 from the inlet-side capillary member 55 similarly to the buffer solution, and thus the buffer solution is replaced with the sample solution inside the channel 57.

Even in this case, since the excitation electrodes 42A and 42B are symmetrically formed when viewed from the inlet side to the outlet side of the channel 57, these excitation electrodes 42A and 42B equally receive a pressure variation by replacement of the liquid inside the channel 57. Thus, the oscillation frequencies of the first vibrating region 61 and the second vibrating region 62 vary all together with one another due to the pressure variation. When the sample solution includes the sensing object, the adsorbing film 46 on the excitation electrode 42A adsorbs this sensing object. On the other hand, the sensing object is not adsorbed on the excitation electrode 42B. This decreases the frequency corresponding to the amount of adsorption of the sensing object to the adsorbing film 46 and varies F1-F2. Thus, this ensures determination of presence/absence of the sensing object based on the variation of F1-F2. A relational expression of variation amounts of difference of the oscillation frequencies F1-F2 and densities of the sensing object in the sample solution may be obtained in advance to calculate the density of the sensing object in the sample solution using this relational expression and a variation amount in the difference of the oscillation frequencies obtained by measurement.

According to the above-described embodiment, the top surface side of the crystal resonator 4, which includes the adsorbing film 46 that absorbs the sensing object on the excitation electrodes 42A and 42B, is pressed with the channel forming member 5 using the upper-side cover body 21 from the top surface side to form the channel 57, which runs on the top surface side of the crystal resonator 4 from one end side to the other end side. The depressed portion 84 is disposed on the top surface of the channel forming member 5 so as to be opposed to the channel 57. The crush margins 81 and 82, which buffers a pressure by being deformed by the pressure, in the peripheral areas of the through holes 52 and 53 on the top surface of the channel forming member 5. Therefore, even in the case where the upper-side cover body 21 has a distortion or an inclination, a deformation of the channel 57 is inhibited when the channel forming member 5 is pressed. Accordingly, the sample solution stably flows in the channel to enhance a measurement sensitivity.

Furthermore, disposing the crush margin 83 on the lower surface side of the surrounding portion 51 of the channel forming member 5 improves the adhesion of the channel forming member 5 to the crystal resonator 4. The disclosure may dispose a depressed portion in a portion in contact with the ceiling portion 100 of the channel forming member 5 of the pressing portion 90. In this case, when the channel forming member 5 is pressed by the pressing portion 90, a pressure on the ceiling portion 100 is reduced and the channel 57 is not collapsed, thus providing a similar effect.

While in the above-described example, the surrounding portion 51 is disposed to contact the crystal resonator 4, the surrounding portion 51 may be disposed to contact the wiring board 3. In this case, the crush margin 83 is simply disposed to project by 0.05 mm from a surface of the surrounding portion 51 in contact with the wiring board 3 when the upper-side cover body 21 and the lower-side case body 22 are locked together and the channel forming member 5 is pressed against the wiring board 3.

The invention claimed is:

1. A sensing sensor comprising:
   a wiring board having one surface side on which a first depressed portion is formed, wherein the first depressed portion is in the one surface side of the wiring board;
   a piezoelectric resonator including a piezoelectric piece on which an excitation electrode electrically connected to a conductive path of the wiring board is disposed, the piezoelectric resonator having one surface side on which an adsorbing film that adsorbs a sensing object in a sample solution is formed, the piezoelectric resonator being secured to the wiring board in a state where a vibrating region is opposed to the first depressed portion to cover the first depressed portion;

a channel forming member disposed to cover a region in the one side of the wiring board including the piezoelectric resonator, the channel forming member forming a channel between the piezoelectric resonator and the channel forming member, the channel communicating with an injection port of the sample solution; and a pressing member that presses a surface on an opposite side of the wiring board in the channel forming member to press the channel forming member against the wiring board, wherein the sensing sensor is configured to form a clearance between the pressing member and a second depressed portion on an opposite side of the channel in the channel forming member to prevent the channel from being collapsed when the pressing member presses the channel forming member.

2. The sensing sensor according to claim 1, comprising a crush margin that buffers a pressure by changing a shape thereof due to a pressure of the pressing member on a surface on the opposite side of the channel in the channel forming member to prevent the channel from being collapsed when the pressing member presses the channel forming member.

3. The sensing sensor according to claim 1, comprising a crush margin disposed on a surface on the wiring board side in the channel forming member, the crush margin being disposed to project from a surface contacting one side of the surfaces of the wiring board including the piezoelectric resonator in the channel forming member when the pressing member presses the channel forming member.

* * * * *